(12) United States Patent
Batayneh et al.

(10) Patent No.: US 9,581,575 B2
(45) Date of Patent: Feb. 28, 2017

(54) SAFETY SYSTEM FOR DETECTION AND ELIMINATION OF TOXIC GASES

(75) Inventors: Wafa Mahmoud Batayneh, Irbid (JO); Mohammad Abdel-Kareem Jaradat, Irbid (JO); Omar Mefleh Al-Araidah, Irbid (JO)

(73) Assignee: JORDAN UNIVERSITY OF SCIENCE AND TECHNOLOGY (JO)

( * ) Notice: Subject to any disclaimer, the term of this patent is extended or adjusted under 35 U.S.C. 154(b) by 1218 days.

(21) Appl. No.: 13/451,143

(22) Filed: Apr. 19, 2012

(65) Prior Publication Data
US 2013/0281004 A1 Oct. 24, 2013

(51) Int. Cl.
| F24F 11/04 | (2006.01) |
| G01N 33/00 | (2006.01) |
| F24F 11/00 | (2006.01) |
| G08B 21/14 | (2006.01) |

(52) U.S. Cl.
CPC ........ *G01N 33/004* (2013.01); *F24F 11/0009* (2013.01); *F24F 11/0079* (2013.01); *G08B 21/14* (2013.01); *F24F 2011/0026* (2013.01); *F24F 2011/0027* (2013.01); *Y02B 30/746* (2013.01); *Y02B 30/78* (2013.01)

(58) Field of Classification Search
CPC ............... F24F 11/0009; F24F 11/0027; F24F 11/0026; F24F 11/0079; F24F 11/0008; F24F 2011/0026; F24F 2011/0027; G08B 21/14; G01N 33/004; Y02B 30/746; Y02B 30/78
USPC .................................. 454/343, 229, 353, 370
See application file for complete search history.

(56) References Cited

U.S. PATENT DOCUMENTS

| 4,357,602 A * | 11/1982 | Lemelson ............... G08B 25/10 340/524 |
| 5,261,596 A * | 11/1993 | Tachibana ............. F24F 11/0009 165/248 |
| 5,292,280 A * | 3/1994 | Janu et al. ..................... 454/229 |
| 6,102,793 A * | 8/2000 | Hansen .......................... 454/342 |
| 6,241,950 B1 * | 6/2001 | Veelenturf ............... G01N 1/26 422/537 |

(Continued)

OTHER PUBLICATIONS

Carbon Monoxide—Health Effects, The Engineering ToolBox, Mar. 17, 2010, https://web.archive.org/web/20100317100716/http://www.engineeringtoolbox.com/carbon-monoxide-d_893.html.*

*Primary Examiner* — Gregory Huson
*Assistant Examiner* — Dana Tighe
(74) *Attorney, Agent, or Firm* — Kelly Kordzik; Matheson Keys Daffer & Kordzik PLLC

(57) ABSTRACT

There is provided a safety system comprising at least one gas detector for detecting presence and concentration of at least one toxic gas inside the target space and for generating corresponding analog signals; (2) an analog-to-digital converter (ADC) connected to the at least one gas detector for converting the analog signals into digital signals; (3) a controller connected to the ADC for receiving the digital signals and generating commands as a function of pre-programmed instructions; (4) at least one exhaust fan connected to the controller for receiving the commands and operating as a function thereof for exhausting the at least one toxic gas outside the target space; and (5) at least one draught fan connected to the controller for receiving the commands and operating as a function thereof for generating a flow of air inside target space.

19 Claims, 3 Drawing Sheets

(56) References Cited

U.S. PATENT DOCUMENTS

| | | | | |
|---|---|---|---|---|
| 7,104,460 | B2 * | 9/2006 | Masen | F23N 3/002 |
| | | | | 236/11 |
| 8,147,302 | B2 * | 4/2012 | Desrochers | F24F 3/044 |
| | | | | 340/632 |
| 2001/0025610 | A1 * | 10/2001 | Weber | 123/41.12 |
| 2007/0181000 | A1 * | 8/2007 | Wilson et al. | 96/134 |
| 2008/0188173 | A1 * | 8/2008 | Chen | F04D 27/004 |
| | | | | 454/239 |
| 2010/0252451 | A1 * | 10/2010 | Warburton | 205/779.5 |
| 2012/0263870 | A1 * | 10/2012 | Hunter | G01N 33/004 |
| | | | | 427/125 |

* cited by examiner

SAFETY SYSTEM FOR DETECTION AND ELIMINATION OF TOXIC GASES

FIELD OF THE INVENTION

The field of the present invention relates to safety systems and devices for detection and elimination of toxic gases in naturally ventilated environments, and more particularly a system used to restrain $CO_2$ and CO resulting of the combustion of fossil fuel using fuzzy controllers.

BACKGROUND OF THE INVENTION

Gas poisoning as a result of fuel-burning inside closed areas is responsible of the lives of many people worldwide. Toxic gases generated from fuel-burning include $CO_2$ and CO. Since these gases are toxic and can cause death, and CO has no smell or odor making such gas hard to detect by human beings, as well as $CO_2$, while the difference is that the latter has a sour taste and stinging effect at high concentrations, thus, numerous conventional apparatuses and methods for the detection of such gases have been suggested in the past.

Among these traditional apparatuses, there were suggested devices for detecting toxic gases and ventilating areas containing these gases, such that sensors of toxic gases (e.g. $O_2$, CO, $CO_2$, $H_2O$ vapor, $N_2$, and other poisonous gases) inside and outside a building are connected to motors which control the starting and stopping of ventilating fans as well as the opening and closing of a tilting window. These devices respond to departures of the air quality from between upper and lower thresholds. It can be programmed to operate periodically and to exclude smog, offensive smells, rain and gales. These devices can be coupled to alarm systems.

Other traditional devices include environment intelligent regulation and control devices, generally comprising an intelligent environment controller, an air conditioner, a humidifier, a temperature sensor, a $CO_2$ sensor, a fuel gas sensor, an electrostatic precipitator and a ventilating mechanism. The air conditioner, the humidifier, the temperature sensor, the $CO_2$ sensor, the fuel gas sensor, the electrostatic precipitator and the ventilating mechanism are connected with the intelligent environment controller through a data line. The ventilating mechanism consists of an exhaust fan, a draught fan, a heat exchange jacket wind pipe and an electric wind door. The exhaust fan and the draught fan are communicated with the outdoor environment through an air-vent. One end parts of an air inlet channel and an air outlet channel in the heat exchange jacket wind pipe are respectively communicated with the air-vents at which the exhaust fan and the draught fan are located and the other end parts are located indoors and communicate with the indoor environment. Each air channel opening is provided with the electric wind door.

Since the prior art ventilating and gas detecting devices used either one ventilating fan to ventilate an area while detecting more than one gas, or two ventilating fans while detecting only one toxic gas, the overall efficiencies of such devices are substandard and needs to be enhanced.

SUMMARY OF THE INVENTION

It is therefore an object of the present invention to provide a device that overcome the above drawbacks.

The present invention provides a device used to restrain emission of gases in naturally ventilated environments, such device utilizes a fuzzy Poka-Yoke controller to control the concentration levels of $CO_2$ and CO gases formed due to the combustion of fossil fuels.

The device comprises: a target area; two DC motorized ventilating fans, one exhaust fan that sucks the polluted air outside said area, and a draught fan that generates fresh air inside such area. Such exchange of air provides access of poisoned victims to fresh air until they evacuate the place or help arrives. The device of the present invention also comprises: A fuzzy controller to control the operation as well as the duty cycle of such fans; two Poka-Yoke gas detecting sensors, one for detecting the concentration level of $CO_2$ in air, and the other for detecting the concentration level of CO in air; and an analog-to-digital converter in order to convert the analog values taken from said sensors into digital values such that they are compatible with said controller.

Said ventilating fans capacities are selected depending on the cubic volume of said target area, the density of air, and the number of air exchanges per hour. Said fans are distant mounted in order to prevent short-circuit circulation of air, and are mounted at an air inlet; basically a window or a ventilation shaft.

Since the system of the present invention is a multi-input multi-output system (MIMO), a fuzzy controller is put in place for controlling the duty cycle and speed of said ventilating fans because such controller is one of the most suitable controllers for controlling MIMO systems.

Therefore, as a first aspect of the invention, there is provided a safety system comprising at least one gas detector for detecting presence and concentration of at least one toxic gas inside the target space and for generating corresponding analog signals; an analog-to-digital converter (ADC) connected to the at least one gas detector for converting the analog signals into digital signals; a controller connected to the ADC for receiving the digital signals and generating commands as a function of pre-programmed instructions; at least one exhaust fan connected to the controller for receiving the commands and operating as a function thereof for exhausting the at least one toxic gas outside the target space; and at least one draught fan connected to the controller for receiving the commands and operating as a function thereof for generating a flow of air inside target space.

Preferably, the numbers of the at least one gas detector and the at least one exhaust and draught fans are determined as a function of physical dimensions of the target space.

Preferably, the at least one gas detector comprises a CO detector and a $CO_2$ detector.

Preferably, the CO and $CO_2$ detectors comprise Poka-Yoke gas sensors having sensitivity ranges.

Preferably, the controller is pre-programmed to categorise the received signals into five concentration ranges, as a function of the detected concentration of the at least one gas, including low, low-medium, medium, medium-high, and high.

Preferably, the concentration ranges are normalized as a function of the sensitivity ranges of the sensors.

Preferably, the controller is a fuzzy controller.

Preferably, the fuzzy controller controls operation and speed of the exhaust and draught fans according to fuzzy expert rules and warning alerts.

Preferably, the exhaust and draught fans are DC motorized.

Preferably, the exhaust fan exhausts polluted air from inside the target space to outside the target space, and wherein the draught fan generates fresh air inside the target space.

Preferably, the exhaust and draught fans have respectively exhaust and draught capacities determined as a function of volume of the target space, density of air inside the target space, and frequency of air exchanges required.

Preferably, the fans operate at five different ranges of speed, including low, medium-low, medium, medium-high, and high.

Preferably, the controller commands comprise desired ranges of speed of the exhaust and draught fans, corresponding to the concentration ranges.

Preferably, the exhaust and draught fans are mounted in accordance with a spatial configuration to prevent short-circuit circulation of air.

Preferably, the spatial configuration is determined as a function of exhaust and draught capacities of the exhaust and draught fans and as a function of physical dimensions of the target space.

Preferably, the spatial configuration comprise an appropriate distance between the exhaust and draught fans.

Preferably, the fans are configured to be mounted on air inlets.

Preferably, the air inlets are selected from the group consisting of a window and a ventilation shaft.

BRIEF DESCRIPTION OF THE DRAWINGS

Further features and advantages of the present invention will become apparent from the following detailed description, taken in combination with the appended drawings, in which.

DETAILED DESCRIPTION OF THE INVENTION

Figure 1:
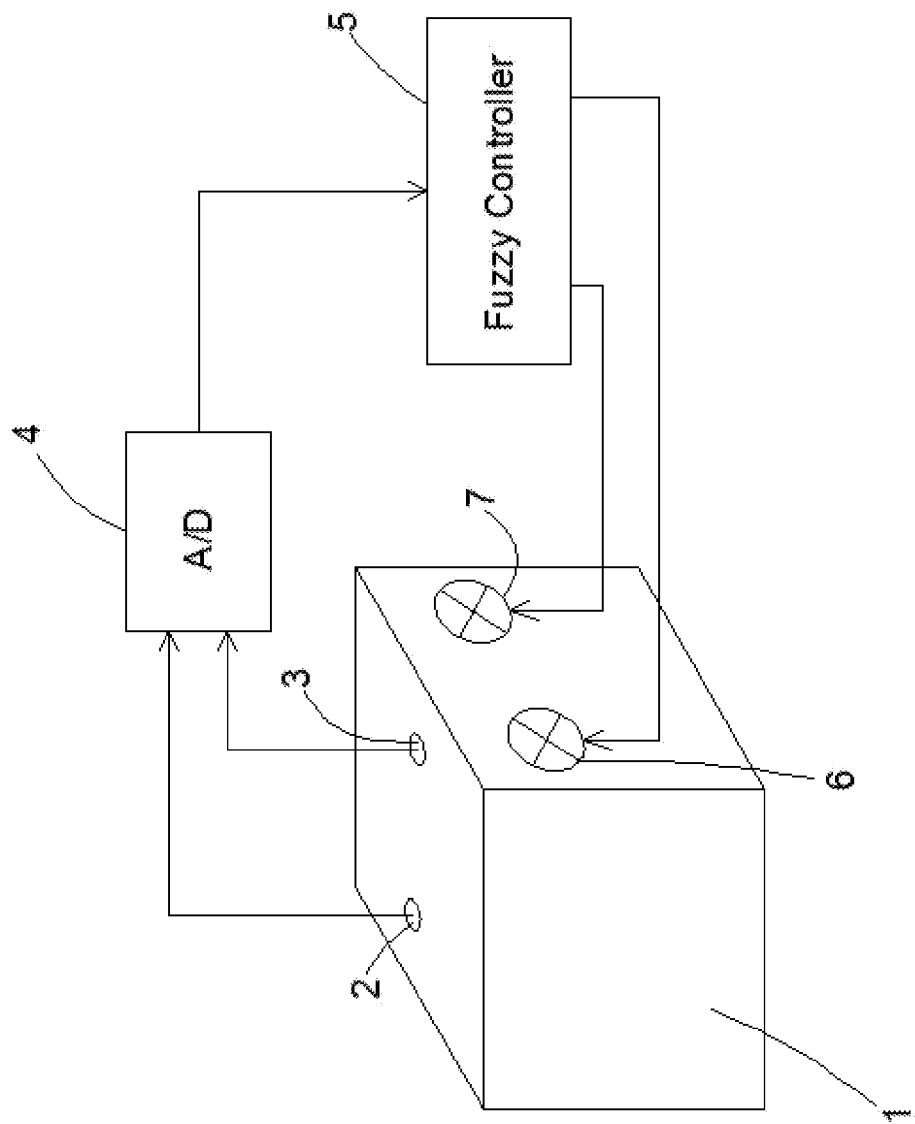
FIG. 1 is a block diagram of a system configured according to the preferred embodiment of the present invention.
Figure 2:
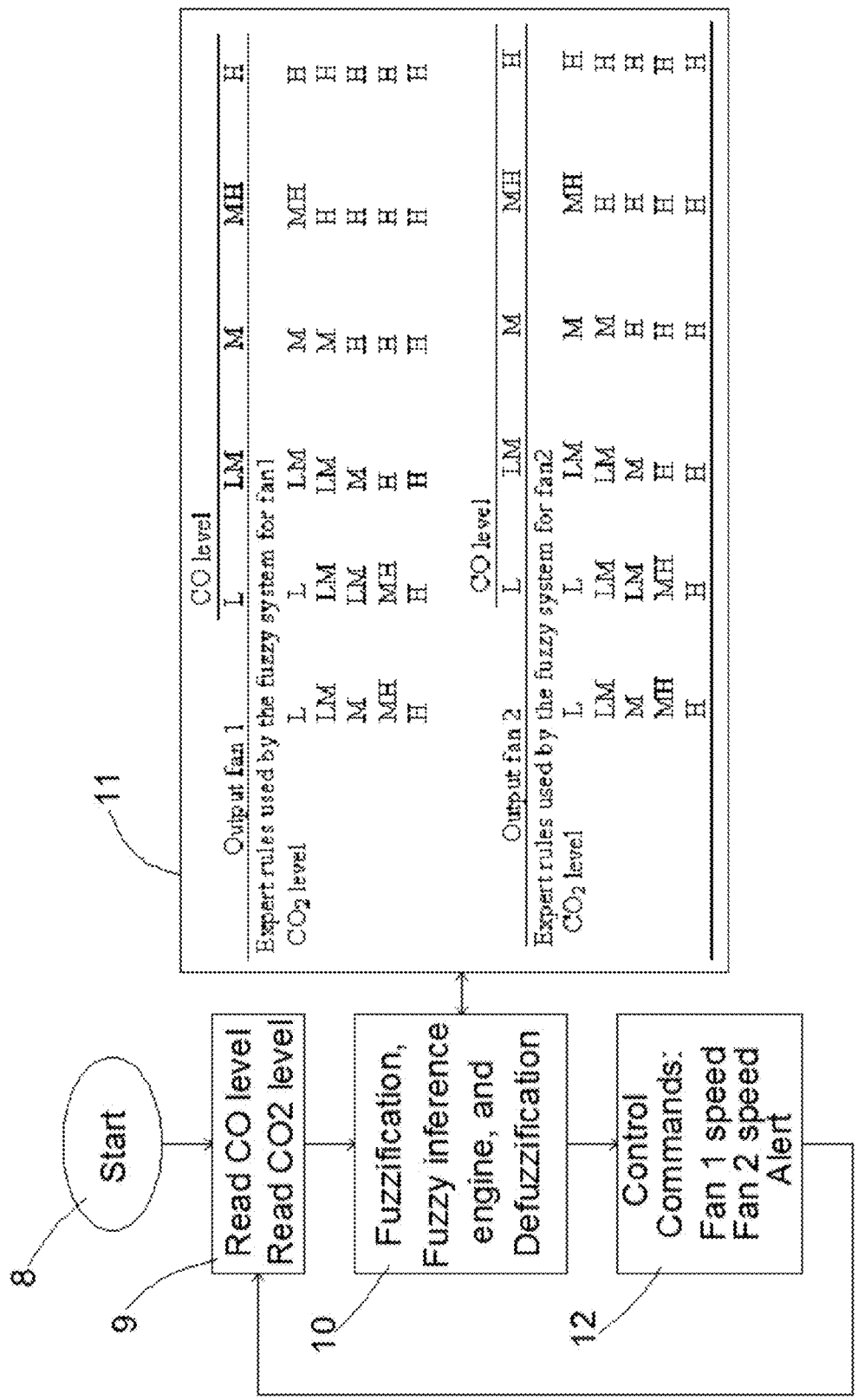
FIG. 2 is a flow chart illustrating the operating steps of a fuzzy controller configured according to the preferred embodiment of the present invention.
Figure 3:
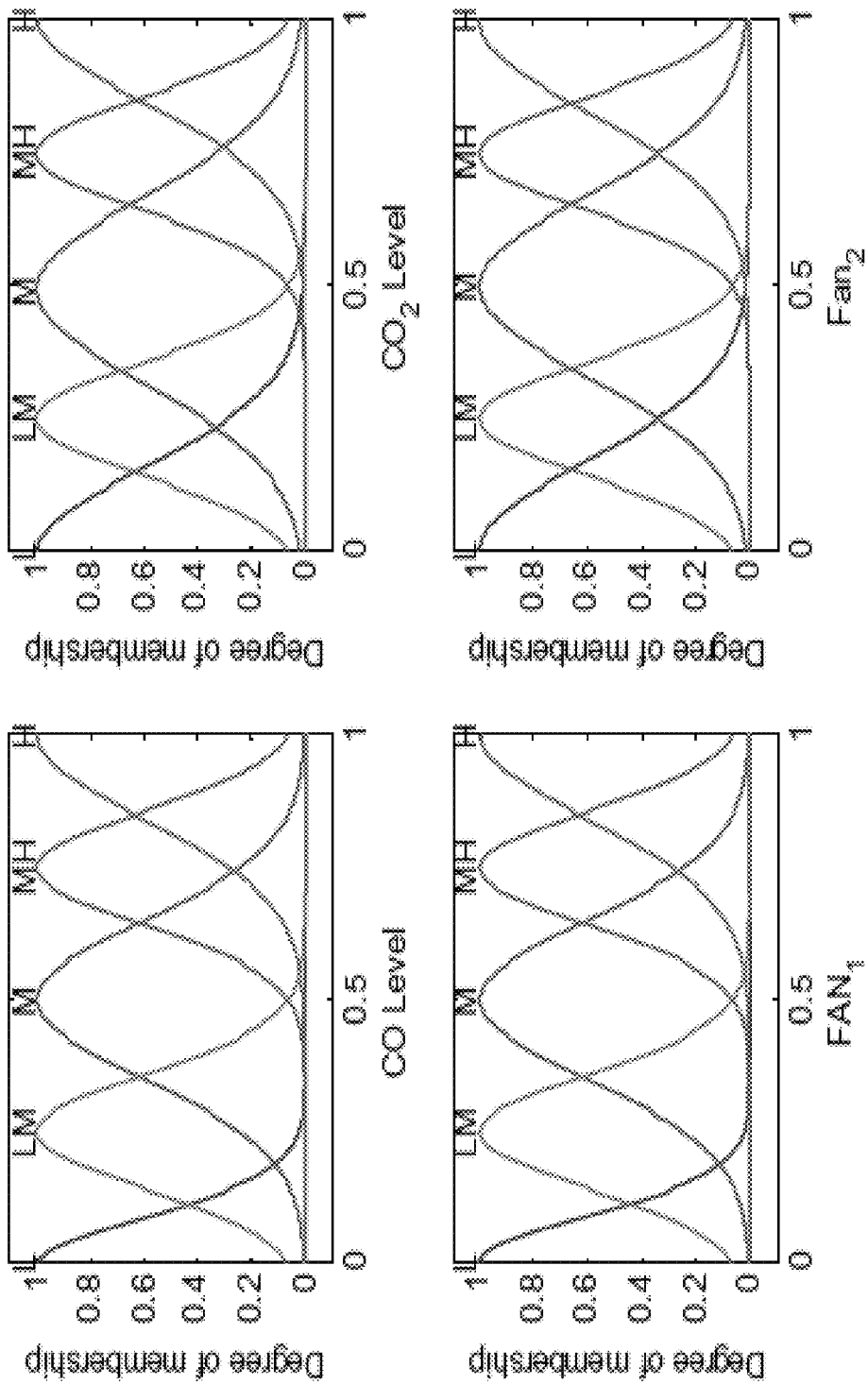
FIG. 3 is a signal chart illustrating membership functions presenting the ranges of input and output variables configured according to the preferred embodiment of the present invention.

FIG. 1 illustrates a ventilation device configured according to a preferred embodiment of the present invention. FIG. 2 depicts a flow chart of the desired instructions performed by a fuzzy controller configured according to the present invention in order to achieve the required tasks. FIG. 3 depicts a signal chart of the membership functions presenting the ranges of input and output variables.

As illustrated in FIG. 1, the device in accordance with the preferred embodiment of the present invention comprises: A target space 1; a CO gas sensor 2 for sensing and detecting the CO gas concentration level; a $CO_2$ gas sensor 3 for sensing and detecting the $CO_2$ concentration level; an analog-to-digital converter 4, wherein such converter converts the analog feedback signals obtained from said sensors 2 and 3 into digital feedback values so that these feedback values are compatible with fuzzy controllers; a fuzzy controller 5, wherein such controller can be implemented using a microcontroller in order to control the duty cycle and thus the speed of the exhaust and draught fans, activate warning alerts when the concentration level/levels of one or both said gas/gases is/are high, and deactivate such alerts when such level/levels fall/falls down; an exhaust fan 6 for the suction of polluted air outside said area; and a draught fan 7 for generating fresh air propelled inside such area, wherein such fans operate at five different speeds: low (L), low-medium (LM), medium (M), medium-high (MH), and high (H). These speeds vary as the concentration levels of CO and $CO_2$ gases change. Such concentration levels have also five ranges: low (L), low-medium (LM), medium (M), medium-high (MH), and high (H).

The numerical values of the speeds corresponding to: low, low-medium, medium, medium-high, and high are normalized based on the maximum speed of any fan, and the concentration level ranges of said CO and $CO_2$ gases corresponding to: low, low-medium, medium, medium-high, and high ranges are normalized based on the sensitivity range of any sensor as shown in FIG. 3. Table 1 presents the approximated levels of the gases and the time required to exchange the air before occupants suffer from poisoning symptoms.

TABLE 1

|  | Level | PPM | Time to evacuate |
| --- | --- | --- | --- |
| CO | L | <400 | <2 hr |
|  | LM | <800 | 45 min |
|  | M | <1600 | 20 min |
|  | MH | <2500 | <15 min |
|  | H | >3000 | <5 min |
| CO2 | L | <2000 | <3 hr |
|  | LM | <5000 | <2 hr |
|  | M | <10000 | <1 hr |
|  | MH | <14000 | <25 min |
|  | H | >30000 | <10 min |

In the preferred embodiment of the present invention, said gas sensors 2 and 3 sense the presence of CO and $CO_2$ and detect their concentration levels inside said target space, then, said analog-to-digital converter 4 reads the feedback signals of such sensors and convert them into digital ones, after that, said fuzzy controller 5 reads such digital values (such values are the inputs of the controller) and performs the desired set of instructions shown in FIG. 2. Finally, said controller 5 outputs the processed data which controls the operation and speed of said exhaust and draught fans 6 and 7 respectively.

The microcontroller includes a central processing unit; discrete input and output bits; input and output ports; clock generator; analog-to-digital converters; volatile memory (RAM) for data storage; and ROM, EPROM, EEPROM or Flash memory for program and operating parameter storage. Microcontroller models including such features are available and known to those skilled in the art, the microcontroller incorporated in the discussed embodiment of the present invention may be anyone of them.

With the aid of the Fuzzy Expert Rules shown in Table 2 below, which are used by the fuzzy system to control the gas level, the flow chart of the fuzzy controller is made as shown in FIG. 2.

TABLE 2

Fuzzy rules applied to gas level control

Sample linguistic rules

IF $CO_2L$ is L AND COL is L THEN $FS_1$ is L AND $FS_2$ is L
IF $CO_2L$ is L AND COL is M THEN $FS_1$ is M AND $FS_2$ is M
IF $CO_2L$ is L AND COL is MH THEN $FS_1$ is H AND $FS_2$ is MH
IF $CO_2L$ is H AND COL is H THEN $FS_1$ is H AND $FS_2$ is H

|  | CO level | | | | |
| --- | --- | --- | --- | --- | --- |
|  | L | LM | M | MH | H |
| Output fan 1 Expert rules used by the fuzzy system for fan1 | | | | | |
| $CO_2$ level  L | L | LM | M | MH | H |
| LM | LM | LM | M | H | H |
| M | LM | M | H | H | H |
| MH | MH | H | H | H | H |
| H | H | H | H | H | H |

TABLE 2-continued

Fuzzy rules applied to gas level control

Output fan 2
Expert rules used by the fuzzy system for fan2

| $CO_2$ level | | | | | |
|---|---|---|---|---|---|
| L | L | LM | M | MH | H |
| LM | LM | LM | M | H | H |
| M | LM | M | H | H | H |
| MH | MH | H | H | H | H |
| H | H | H | H | H | H |

Having described the overall hardware configuration of the system in conjunction with the schematic diagram of FIG. 1, reference is now made to the flow chart of FIG. 2 for understanding the operational steps of said fuzzy controller implemented using the microcontroller. The specific source code and object code are machine-dependent, and therefore, it is not helpful to a full understanding of the invention to set out the detailed coding employed. Persons skilled in the art of programming who have the benefit of the forgoing description and explanation as well as the accompanying flow chart of the software will be able to develop the code applicable to the particular microcontroller chip employed.

Referring to FIG. 2, the operation starts by installing and initializing the hardware (Block 8); detecting the levels of CO and $CO_2$ gases (Block 9) by said CO and $CO_2$ gas sensors 2 and 3; then, feeding such levels to said fuzzy controller 5 (Block 10) and performing the actions of fuzzification, fuzzy inference, and defuzzification according to fuzzy rules (Block 11 and also shown in Table 2) by said controller 5. After that, the outputs of the control commands are generated by said controller 5 (Block 12) for the purpose of controlling the speeds of said fans 6 and 7; activating warning alerts when the level/levels of one or both of said gases is/are high; and deactivating such alerts when the levels of gases are low, wherein such operation procedure is recurrent polling procedure.

CO and $CO_2$ gases can come from the combustion of fossil fuel, especially in cold weather; since most heating systems utilize the combustion of such fuel as a source of heat.

While the invention has been described in details and with reference to specific embodiments thereof, it will be apparent to one skilled in the art that various additions, omissions and modifications can be made without departing from the spirit and scope thereof.

While illustrated in the block diagrams as groups of discrete components communicating with each other via distinct data signal connections, it will be understood by those skilled in the art that the preferred embodiments are provided by a combination of hardware and software components, with some components being implemented by a given function or operation of a hardware or software system, and many of the data paths illustrated being implemented by data communication within a computer application or operating system. The structure illustrated is thus provided for efficiency of teaching the present preferred embodiment.

Although the above description contains many specificities, these should not be construed as limitations on the scope of the invention but is merely representative of the presently preferred embodiments of this invention. The embodiment(s) of the invention described above is(are) intended to be exemplary only. The scope of the invention is therefore intended to be limited solely by the scope of the appended claims.

The invention claimed is:

1. A safety system comprising:
    at least one gas detector for detecting presence and concentration of at least one toxic gas inside a target space and for generating corresponding analog signals;
    an analog-to-digital converter (ADC) connected to said at least one gas detector for converting said analog signals into digital signals;
    a controller connected to said ADC for receiving said digital signals and generating commands as a function of pre-programmed instructions;
    at least one exhaust fan connected to said controller for receiving said commands and operating as a function thereof for exhausting said at least one toxic gas outside said target space; and
    at least one draught fan connected to said controller for receiving said commands and operating as a function thereof for generating a flow of air inside said target space,
    wherein the numbers of said at least one gas detector and said at least one exhaust and draught fans are determined as a function of physical dimensions of said target space.

2. The system as claimed in claim 1, wherein said at least one gas detector comprises a CO detector and a $CO_2$ detector.

3. The system as claimed in claim 2, wherein said CO and $CO_2$ detectors comprise Poka-Yoke gas sensors having sensitivity ranges.

4. The system as claimed in claim 3, wherein said controller is pre-programmed to categorise said received signals into five concentration ranges, as a function of the detected concentration of said at least one gas, including low, low-medium, medium, medium-high, and high.

5. The system as claimed in claim 4, wherein said concentration ranges are normalized as a function of said sensitivity ranges of said sensors.

6. The system as claimed in claim 1, wherein said controller is a fuzzy controller.

7. The system as claimed in claim 1, wherein said exhaust and draught fans are DC motorized.

8. The system as claimed in claim 1, wherein said exhaust fan exhausts polluted air from inside said target space to outside said target space, and wherein said draught fan generates fresh air inside said target space.

9. The system as claimed in claim 1, wherein said exhaust and draught fans are mounted in accordance with a spatial configuration to prevent short-circuit circulation of air.

10. The system as claimed in claim 1, wherein said at least one gas detector is disposed within said target space.

11. The system as claimed in claim 10, wherein said at least one gas detector detects the concentration levels of CO and $CO_2$ gases in said target space.

12. A safety system comprising:
    at least one gas detector for detecting presence and concentration of at least one toxic gas inside a target space and for generating corresponding analog signals;
    an analog-to-digital converter (ADC) connected to said at least one gas detector for converting said analog signals into digital signals;
    a fuzzy controller connected to said ADC for receiving said digital signals and generating commands as a function of pre-programmed instructions;
    at least one exhaust fan connected to said fuzzy controller for receiving said commands and operating as a function thereof for exhausting said at least one toxic gas outside said target space; and at least one draught fan connected to said fuzzy controller for receiving said commands and operating as a function thereof for generating a flow of air inside said target space, wherein said fuzzy controller controls operation and speed of said exhaust and draught fans according to fuzzy expert rules and warning alerts.

13. A safety system comprising:

at least one gas detector for detecting presence and concentration of at least one toxic gas inside a target space and for generating corresponding analog signals;

an analog-to-digital converter (ADC) connected to said at least one gas detector for converting said analog signals into digital signals;

a controller connected to said ADC for receiving said digital signals and generating commands as a function of pre-programmed instructions;

at least one exhaust fan connected to said controller for receiving said commands and operating as a function thereof for exhausting said at least one toxic gas outside said target space; and at least one draught fan connected to said controller for receiving said commands and operating as a function thereof for generating a flow of air inside said target space, wherein said exhaust fan exhausts polluted air from inside said target space to outside said target space, and wherein said draught fan generates fresh air inside said target space, wherein said exhaust and draught fans have respectively exhaust and draught capacities determined as a function of volume of said target space, density of air inside said target space, and frequency of air exchanges required.

14. The system as claimed in claim 13, wherein said fans operate at five different ranges of speed, including low, medium-low, medium, medium-high, and high.

15. The system as claimed in claim 14, wherein said controller commands comprise desired ranges of speed of said exhaust and draught fans, corresponding to said concentration ranges.

16. A safety system comprising:

at least one gas detector for detecting presence and concentration of at least one toxic gas inside a target space and for generating corresponding analog signals;

an analog-to-digital converter (ADC) connected to said at least one gas detector for converting said analog signals into digital signals;

a controller connected to said ADC for receiving said digital signals and generating commands as a function of pre-programmed instructions;

at least one exhaust fan connected to said controller for receiving said commands and operating as a function thereof for exhausting said at least one toxic gas outside said target space; and at least one draught fan connected to said controller for receiving said commands and operating as a function thereof for generating a flow of air inside said target space, wherein said exhaust and draught fans are mounted in accordance with a spatial configuration to prevent short-circuit circulation of air, wherein said spatial configuration is determined as a function of exhaust and draught capacities of said exhaust and draught fans and as a function of physical dimensions of said target space.

17. The system as claimed in claim 16, wherein said spatial configuration comprise an appropriate distance between said exhaust and draught fans to prevent short-circuit circulation of air between the fans within said target space.

18. The system as claimed in claim 17, wherein said fans are configured to be mounted on air inlets.

19. The system as claimed in claim 18 wherein said air inlets are selected from the group consisting of a window and a ventilation shaft.

* * * * *